US006458340B1

(12) United States Patent
Ibsen et al.

(10) Patent No.: US 6,458,340 B1
(45) Date of Patent: Oct. 1, 2002

(54) DESENSITIZING BLEACHING GEL

(75) Inventors: Robert L. Ibsen; Alan Mathews, both of Santa Maria; Thomas C. Chadwick, Nipoma; Xinyi Yu, Santa Maria, all of CA (US)

(73) Assignee: Den-Mat Corporation, Santa Maria, CA (US)

( * ) Notice: Subject to any disclaimer, the term of this patent is extended or adjusted under 35 U.S.C. 154(b) by 0 days.

(21) Appl. No.: 09/438,663

(22) Filed: Nov. 12, 1999

Related U.S. Application Data

(60) Provisional application No. 60/108,441, filed on Nov. 13, 1998, and provisional application No. 60/099,673, filed on Sep. 10, 1998.

(51) Int. Cl.$^7$ ............................ A61K 7/20; A61K 7/16; A61K 33/40; A61C 5/00
(52) U.S. Cl. ........................ 424/53; 424/613; 424/616; 424/49; 106/35; 433/215; 433/216
(58) Field of Search .................... 424/49–58

(56) References Cited

U.S. PATENT DOCUMENTS

| | | | | |
|---|---|---|---|---|
| 3,863,006 A | * | 1/1975 | Hodosh ........................ | 424/49 |
| 4,988,500 A | * | 1/1991 | Hunter et al. .................. | 424/53 |
| 5,264,205 A | * | 11/1993 | Kelly ........................... | 424/53 |
| 5,631,000 A | * | 5/1997 | Pellico ......................... | 424/53 |
| 5,718,886 A | * | 2/1998 | Pellico ......................... | 424/53 |
| 5,785,527 A | * | 7/1998 | Jensen et al. .................. | 424/53 |
| 5,851,512 A | * | 12/1998 | Fischer ......................... | 424/49 |
| 5,855,870 A | * | 1/1999 | Fischer ......................... | 424/49 |
| 5,858,332 A | * | 1/1999 | Jensen et al. .................. | 424/53 |
| 5,922,307 A | * | 7/1999 | Montgomery ................ | 424/53 |
| 5,985,249 A | * | 11/1999 | Fischer ......................... | 424/49 |
| 6,036,943 A | * | 3/2000 | Fischer ......................... | 424/49 |
| 6,108,850 A | * | 8/2000 | McLaughlin ............... | 15/167.1 |

FOREIGN PATENT DOCUMENTS

GB  1267618 A  * 3/1972

OTHER PUBLICATIONS

Effectiveness, Side Effects & Long–Term Status of Nightguard Vital Bleaching, Haywood et al., JADA, vol. 125, pp. 1219–1226, Sep. 1994.

Clinical Evaluation of A Combined In–Office And At–Home–Applied Bleaching Agent, C.A. Munoz et al., pp. 144+, Journal of Dental Research, vol. 79 (1999) (abstract).

U.S. application No. 09/392,475.

U.S. Provisional application No. 60/099,673.

A Superior Desensitizer—Potassium Nitrate, Milton Hadesh, JADA, vol. 88, pp. 851–832, Apr., 1974.

Hodosh (I)J. Amer. Dent. Assn. 88(4) 831–832 a Superior Desensitizer—Potassium Nitrate, 1974.*

Haywood et al J. Amer. Dent. Assn. 125:1219–1226 Effectiveness, Side Effects and Long Term Status of Nightguard Vital Bleaching (Sensitivity During or After Bleaching), Sep. 1994.*

DenMat Rembrandt XTRA–Comfort Non–Sensitizing Bleaching Gel, 1998. DenMat Website http://www.denmat-.com/main/htm Rembrandt XTRA Comfort–Bleaching System—DenMat Desinsitizing Gel, 1998–1999 copyright.*

Ultradent Products Online Website: http://www.ultradent-.com/ "Opalescence", 1999. Discus Dental Website http://www.discusdental.com, Mar. 13, 2000.*

Rembrandt XTRA–Comfort Den–Mat™Req 2270886 Aug. 17, 1999 Rembrandt XTRA–Comfort Non–Sensitizing Bleaching Gel Extra Strength Mint (Ingredients on Label), Sep. 25, 1998 First Use in Commerce.*

Dentistry Today—Buyers' Guide to Whitening Systems, Dec. 1997.*

\* cited by examiner

*Primary Examiner*—Shep K. Rose

(57) ABSTRACT

A substantially anhydrous gel useful for bleaching teeth comprising: (i) at least 25% by weight of organic polyol; (ii) less than 3% by weight polyacrylic acid thickening agent; (iii) at least 10% by weight carbamide peroxide (or a chemically equivalent amount of another bleaching agent, such as 3% by weight hydrogen peroxide); (iv) neutralizing agent; (v) chelating agents; (vi) desensitizing agent; and (vii) miscellaneous ingredients such as Cirtoxain® and flavorants. The organic polyol is preferably glycerin. The polyacrylic acid thickening agent is preferably a carbomer. The desensitizing agent is preferably potassium nitrate, strontium chloride, potassium citrate, strontium nitrate, or a similarly effective alkali or alkaline earth metal salt of an organic or inorganic acid.

15 Claims, No Drawings

DESENSITIZING BLEACHING GEL

RELATED APPLICATIONS

This application is related to provisional application No. 60/108,441 filed on Nov. 13, 1998. Also this application is a PRO of No. 60/099,673 filed Sep. 10, 1998.

TECHNICAL FIELD

This invention pertains to bleaching gels for use in bleaching teeth. More specifically, this invention relates to substantially anhydrous dental bleaching gels that contain: (i) at least 25% by weight organic polyol; (ii) less than 3% by weight polyacrylic acid thickening agent; (iii) at least 10% by weight carbamide peroxide (or a chemically equivalent amount of another bleaching agent, such as 3% by weight hydrogen peroxide); (iv) neutralizing agent; (v) chelating agents; (vi) desensitizing agent; and (vii) flavorants.

BACKGROUND ART

A gel is a colloid produced by combining a dispersed phase with a continuous phase (i.e., a dispersion medium or matrix) to produce a viscous, jelly-like, semisolid material. In the dental industry, gels are utilized as vehicles for applying a variety of dentifrices, bleaching aids, and fluoride compounds to teeth. A "dental bleaching gel" is a gel that carries a bleaching agent that can be safely applied to teeth.

The thickening agent or gelling agent utilized to form the continuous phase of most dental bleaching gels is selected from carboxymethylcellulose, xanthan gum, carrageenan gum, nonionic surfactants, polyethylene oxide macropolymers such as Polymer H®, and carbomers such as Carbopol® 940. The dispersed phase of most dental bleaching gels is water and/or an organic polyol such as glycerine. The bleaching agents of choice tend to be hydrogen peroxide ($H_2O_2$), or compounds, such as urea peroxide ($CO(NH_2)_2H_2O_2$), that yield hydrogen peroxide in an aqueous environment (such as the mouth).

For example, U.S. Pat. Nos. 5,098,303, 5,234,342, 5,376,006, and 5,725,843, assigned to Ultradent Products, teach water-based bleaching gels that contain 3.5% or more Carbopol® 934P or 940 carbomer, glycerine, and a peroxide such as hydrogen peroxide or carbamide peroxide (urea peroxide). In addition, PROXIGEL®, described in U.S. Pat. No. 3,657,413, is a teeth whitening composition that contains urea peroxide. Finally, Den-Mat Corporation currently sells a dental bleaching gel composition called LIGHTEN GEL that is a glycerine composition containing carbamide peroxide and Carbopol® 940 carbomer in an amount ranging from 0.6 to 11 weight percent.

The dental bleaching agents described above are all effective for whitening teeth. However, the use of bleaching agents such as urea peroxide serves to aggravate hypersensitive teeth and causes a period of discomfort. It would be desirable to develop an improved bleaching agent that is equally effective in whitening teeth and reducing or eliminating the dental hypersensitivity sometimes aggravated by bleaching agents.

There is also an ever present need in the art to develop dental bleaching agents that can be more easily and quickly processed, that employ lesser amounts of thickening agent, and that exhibit superior gel stability. Such gels would be more commercially viable.

SUMMARY OF INVENTION

This invention relates to substantially anhydrous dental bleaching gels that contain: (i) at least 25% by weight organic polyol; (ii) less than 3% by weight polyacrylic acid thickening agent; (iii) at least 10% by weight carbamide peroxide (or a chemically equivalent amount of another bleaching agent, such as 3% by weight hydrogen peroxide); (iv) a neutralizing agent; (v) a desensitizing agent; (vi) chelating agents; and (vii) miscellaneous materials such as Citroxain® and flavorants. Preferably, the desensitizing agent is an alkali or alkaline earth metal salt of an organic or inorganic acid or halide such as potassium nitrate, potassium citrate, strontium nitrate and strontium chloride. The thickening agent is chosen so that even in low amounts it will produce a gel with a desired viscosity. The gel can be processed in an easier and faster fashion and exhibits higher stability. These and other features and advantages of the invention are described in, or are apparent from, the following detailed description of the preferred embodiments. Gels made as described above, but without a chelating agent, will (at higher peroxided concentrations) exhibit instability resulting in release of oxygen gas that can cause packaging leaks.

DESCRIPTION OF THE INVENTION

As stated, the instant invention is directed to substantially anhydrous dental bleaching gels. The gels comprise: (i) organic polyol; (ii) polyacrylic acid thickening agent; (iii) bleaching agent; (iv) a neutralizing agent; (v) desensitizing agent; (vi) chelating agent; and (vii) miscellaneous materials such as Citroxain® and flavorants.

The gel should be water soluble while simultaneously exhibiting sufficient film integrity to avoid disintegrating immediately upon exposure to water (which is a major component of saliva). This is because the utility of a dental bleaching gel is dependant upon its residence time, which is defined herein as the time the dental bleaching gel actually contacts the tooth enamel. It is, therefore, desirable to minimize the presence of water in the gel. Preferably, the gel is substantially anhydrous.

The term "substantially anhydrous" means that water is not a necessary component of the invention and is never deliberately added in and of itself. However, the term "substantially anhydrous" does not prevent the presence of minor amounts of water in some of the gel components. Small amounts of water are not overly detrimental.

The dispersed phase of the gel is an organic polyol. Examples of acceptable organic polyols are propylene glycol and glycerin. Glycerin is the most preferred organic polyol component. Glycerin ($C_3H_8O_3$) is a commercially available trihydric alcohol that is also known by the names glycerol, glycyl alcohol, 1,2,3-propanetriol, and trihydroxypropane. Generally, glycerin comes in the form of a clear colorless, odorless syrupy liquid. It is often supplied in a form containing 99.7% glycerin and 0.3% water.

The organic polyol is employed in an amount of at least 25% by weight of the gel. The exact amount of organic polyol employed in the gel will vary in almost direct relation to the amount of bleaching agent employed in the gel. For example, a regular strength dental bleaching gel with approximately 10% by weight carbamide peroxide will include approximately 60% by weight organic polyol, whereas a dental bleaching gel with approximately 40% by weight carbamide peroxide will include approximately 30% by weight organic polyol.

The thickening agent (gelling agent) is present in an amount ranging from 0.25% to 3% by weight of the non-aqueous gel. The thickening agent is a "polyacrylic acid" which means that it is selected from acrylic acid homopolymers and copolymers comprising 90% or more, by weight, polymerized acrylic acid units. The preferred acrylic acid monomer used to make these thickeners is the actual compound "acrylic acid." However, other acrylic acids can also be employed, e.g., methacrylic acid and $C_{1-4}$ alkyl substituted acrylic acid. Other comonomers that may be present in the polymer chain include 10% by weight or less long chain alkyl esters of acrylic acid.

Suitable thickeners include the crosslinked polyacrylic resins sold by B.F. Goodrich under the tradenames Carbopol® 1342, Carbopol® 1382, and Carbopol® ETD™ 2020. Carbopol® Ultrez™ 10 is not as effective but may be used. However, it should be noted that more traditional Carbopol® products, such as Carbopol® 940 and Carbopol® 980 are not satisfactory. The USP-NF, British Pharmacopoeia, United States Adopted Names Council (USAN), and Cosmetic, Toiletries and Fragrance Association (CTFA) have adopted the generic (i.e. non-proprietary) name "carbomer" for the Carbopol® homopolymers. The Japanese Pharmaceutical Exipients list Carbopol® homopolymers as "carboxyvinyl polymer" and "carboxy polymethylene." All of these polymers have the same acrylic acid backbone. The main differences are related to the presence of comonomer and crosslink density. These polymers are either homopolymers of acrylic acid crosslinked with allyl sucrose, polyalkyl ethers of divinyl glycol, or allyl pentaerythritol or similarly crosslinked copolymers of acrylic acid with minor levels of long chain alkyl acrylate comonomers. These polymers swell in water up to 1000 times their original volume (and ten times their original diameter) to form a gel when exposed to a pH environment above 4.0–6.0. Carbopol® thickeners are highly resistant to hydrolysis and oxidation under normal conditions.

Preferred thickeners include Carbopol® ETD™ 2020. This "easy-to-disperse (ETD™)" thickener is an acrylic acid polymer produced using a polymerization aid, and crosslinked with a polyalkenyl polyether. Carbopol® ETD™ 2020 is easier to disperse and mix than other Carbopol® products. The thickener wets quickly and thereby minimizes lumping. By "wet" it is meant that the white particles of polymer fully disappear (disperse) into the mixture. The thickener also hydrates slowly and has a lower viscosity prior to neutralization than other Carbopol® products. Because of the fast wetting nature and low viscosity of the thickener prior to neutralization, vigorous agitation is not necessary for dispersion. The fast wetting nature of the thickener also aids handling. Once the ETD™ resin is neutralized, it provides the type of highly efficient thickening for which Carbopol® resins are known.

Preferred thickeners include Carbopol® 1342, Carbopol® 1382, and Carbopol® ETD™ 2020 where Carbopol® ETD™ 2020 is the most preferred. This thickener is an exceptionally easy-to-disperse polymer that wets even more quickly than the Carbopol ETD™ resins. In fact, Carbopol® Ultrez™ 10 wets without any stirring. For example, a 500 gram dispersion at 0.5% resin (2.5 grams) will take only about 5 minutes to completely wet without mixing. This decreases the time and effort necessary to achieve a smooth dispersion.

One of the discoveries in this invention is that the aforementioned thickening agents are capable of generating a gel even at the low concentrations provided (3% by weight or less) and in the presence of large quantities of salt. Regular thickeners are not as efficient in thickening as Carbopol® 1342, Carbopol® 1382, and Carbopol® ETD™ 2020. In contrast, the use of traditional thickening agents such as carboxymethylcellulose, xanthan gum, carrageenan gum, polyethylene oxide macropolymers such as Polymer H®, and other carbomers such as Carbopol® 940, cannot obtain such a high viscosity when employed in such low concentrations. The viscosity of the gel is very important both for application and effectiveness. If the gel's viscosity is too low, the gel will flow uncontrollably from the dispensing tube and become difficult to manipulate for the purposes of varying or equalizing the bleaching treatment applied to each tooth. More importantly, if the viscosity is too low, the gel is more likely to flow away from the teeth, resulting in reduced residence time. Residence time is the time the dental bleaching gel is actually in contact with the tooth enamel and the effectiveness of a dental bleaching gel is directly proportional to its residence time.

The bleaching agent may be selected from hydrogen peroxide ($H_2O_2$) or any compound that yields hydrogen peroxide when placed in an aqueous medium (such as the mouth). Por example, urea peroxide ($CO(NH_2)_2H_2O_2$) generates hydrogen peroxide when placed in water. Other names for urea peroxide include carbamide peroxide, urea hydrogen peroxide, hydrogen peroxide carbamide and perhydrol urea. Urea peroxide is the most preferred bleaching agent for use in the invention.

Another important discovery incorporated in the invention involves the inclusion of chelating agents such as ethylenediaminetetraacetic acid (EDTA); its metal salts; trans-1,2 diaminocyclohexanetetraacetic acid monohydrate (CDTA), and the like. Most preferably, calcium disodium ethylenediaminetetraacetic acid ($CaNa_2EDTA$) is incorporated at levels from 0.02% to 0.15% by weight of the total formulation. When formulations employing urea peroxide and potassium nitrate (as described previously) are placed into syringes and sealed at the dispensing end, they quite often exhibit peroxide instability which results in a release of gas that forces the plunger from the syringe barrel. The addition of a chelating agents, such as $CaNa_2EDTA$, was shown to greatly reduce this gas release. To illustrate this point, the following gels were prepared:

TABLE 1

Gel A - 28.6% Urea Peroxide Gel without $CaNa_2EDTA$

| Component | % w/w |
|---|---|
| Gycerin | 44.6982 |
| Uea peroxide | 28.6000 |
| Sdium citrate | 13.2600 |
| Ptassium nitrate | 5.0000 |
| Aumina | 4.0000 |
| Carbopol ETD ™ 2020 | 2.2480 |
| Trolamine | 1.4170 |
| Flavor | 0.3678 |
| Papain | 0.3000 |

TABLE 2

Gel B - 28.6% Urea Peroxide Gel with $CaNa_2EDTA$

| Component | % w/w |
|---|---|
| Gycerin | 44.6982 |
| Uea peroxide | 28.6000 |
| Sdium citrate | 13.1725 |
| Ptassium nitrate | 5.0000 |
| Aumina | 4.0000 |
| Carbopol ETD ™ 2020 | 2.2480 |
| Trolamine | 1.4170 |
| Flavor | 0.3678 |

TABLE 2-continued

Gel B - 28.6% Urea Peroxide Gel with CaNa₂EDTA

| Component | % w/w |
|---|---|
| Papain | 0.3000 |
| CaNa₂EDTA | 0.0875 |

These gels were then used to conduct the stability test described in the following table:

TABLE 3

Peroxide Stability of 22% Urea Peroxide Desensitizing Bleaching Gels

| Gel | Temperature | Time (days) | Plunger movement |
|---|---|---|---|
| A (from table 1) | room temp. | 5 days | 0 mm |
| A | room temp. | 14 days | 3 mm |
| A | room temp. | 21 days | 4 mm |
| B (from table 2) | room temp. | 5 days | 0 mm |
| B | room temp. | 14 days | 2 mm |
| B | room temp. | 21 days | 3 mm |
| A | 35° C. | 5 days | 9 mm |
| A | 35° C. | 14 days | 15 mm |
| B | 35° C. | 5 days | 7 mm |
| B | 35° C. | 14 days | 13 mm |

The amount of bleaching agent employed will vary with the reactivity of the bleaching agent and the desired bleaching strength of the gel. For example, it generally takes more urea peroxide than hydrogen peroxide to accomplish an equivalent whitening effect. However, in general, the bleaching agent will be employed in an amount of at least 10% by weight of carbamide peroxide (the lowest strength gels) and in an amount no greater than 50% by weight for the highest strength gels.

In addition to the aforementioned components, a neutralizing agent is added to the non-aqueous gel. The presence of a neutralizing agent is preferred since it serves to further thicken the system. The neutralization agent ionizes the polyacrylic acid thickening agent and generates negative charges along the backbone of the polymer. Repulsions of like charges then cause uncoiling of the polymer into an extended structure. This reaction is rapid and gives almost instantaneous thickening.

The inorganic and organic neutralizing agents which may be employed are bases. Suitable bases include alkali metal hydroxides and ammonium hydroxide, carbonates, alkoxides, oxides, peroxides, superoxides, and water soluble organic amines. Amino acids such as β-alanine and lysine can also be used for neutralization and viscosity modification. Preferred bases include sodium hydroxide, potassium hydroxide, ammonium hydroxide, triethanolamine (TEA), aminomethyl propanol (AMP), 2-amino-2-hydroxymethyl-1,3-propanediol (Tromethamine), tetrahydroxypropyl ethylenediamine, and tris(hydroxymethyl)aminomethane (TRIS). The amount of base utilized is the amount of base necessary to fully neutralize the polyacrylic acid thickener in the gel. This amount of neutralizing agent employed will vary considerably depending on the nature of the base and the amount and equivalent weight of the polyacrylic acid. For example, the following Table 4 sets forth the amount of different bases required to neutralize an identical polyacrylic acid to an appropriate pH of 6.0–7.0:

TABLE 4

Amount of Base Required to Neutralize Polyacrylic Acid

| Base | Relative ratio of base to one part polyacrylic acid by weight |
|---|---|
| Sodium hydroxide (18% solution) | 0.5 |
| Potassium hydroxide (18% solution) | 0.5 |
| Ammonium hydroxide (28% solution) | 0.3 |
| Triethanolamine (TEA) | 2.0 |
| Tromethamine (2-Amino-2-Hydroxymethyl-1,3-propandiol) | 2.0 |
| Aminomethyl propanol (AMP) | 1.5 |
| Tetrahydroxypropyl ethylene diamine | 2.0 |

One of the important discoveries leading to the invention was that the use of certain alkali and alkaline earth metal salts significantly reduces, or completely removes, tooth sensitivity accompanying the use of bleaching agents without hindering their stability or whitening capabilities. "Clinical Evaluation of a Combined In-Office and At-Home Applied Bleaching Agent" at Loma Linda University School of Dentistry, Center for Dental Research, Lima Linda, Calif. by Carlos A. Munoz, James R. Dunn, Yiming Li, and Jay Kim, is hereby incorporated by reference. Preferably, the desensitizing agent is selected from alkali and alkaline earth metal nitrates, citrates, and halides, such as potassium nitrate, potassium citrate, strontium nitrate and strontium chloride. Potassium nitrate at 5% is the most preferred desensitizing agent because it is both highly effective and approved by the United States Food and Drug Administration. Clinical testing has been carried out which shows that sensitivity in the teeth and gums is basically eliminated when one of more of these desensitizing agents are employed in the dental bleaching gel. The desensitizing agents are employed in the amount of at least 0.1%, preferably 0.1 to 10%, and most preferably around 5%, by weight of the dental bleaching gel.

Other ingredients traditionally employed in the dental bleaching art may also be added. For example, the dental bleaching gels of the instant invention may additionally comprise chelating agents and Citroxain® (which is a combination of citric acid, its salts, alumina, papain and flavorants).

If the bleaching gel contains approximately 10% by weight urea (carbamide) peroxide, or an equivalent amount of hydrogen peroxide, it is generally applied by dispensing the gel from a compressible tubular container, syringe, or other device, onto a dental tray. A dental tray is defined herein as any device that is placed over or against one or more teeth. A wide variety of dental trays are taught in the prior art that are suitable for use in the instant invention. For example, the dental tray can be a vacuum formed from a thermoplastic sheet on a dental stone cast of the teeth. Alternatively, the dental tray can a soft plastic that conforms to the shape of the teeth when subjected to heat and pressure (analogous to the mouth guards used in most contact sports). The dental tray is then inserted into the user's mouth in a manner that allows the bleaching agent to contact the user's teeth for extended periods of time, ranging anywhere from thirty minutes to eight hours. The process is repeated several times over a period of days or weeks until the desired degree of whiteness is obtained.

If the dental gel is a higher strength bleaching gel, the soft tissues surrounding the teeth are first covered with a protecting device, e.g., a ligated rubber dam. This is important because the more bleaching agent a dental bleaching gel contains, the more likely it is to burn the soft tissue upon contact. For example, dental bleaching gels containing 40% urea peroxide, or an equivalent amount of hydrogen peroxide, will immediately burn any soft tissue they contact, quickly turning the tissue white.

Next a brush, needle, or some other delivery system is utilized to place the dental bleaching gel described above in contact with the teeth one wishes to bleach. Most patients only request treatment on the labial surfaces of the 6 to 8 front teeth which show most prominently when one smiles.

The dental bleaching gel is then allowed to remain in contact with the teeth for a period of time ranging anywhere from 5 minutes to two hours. Preferably, however, this contact period ranges from 20 to 30 minutes. As stated earlier, the bleaching effect of any dental bleaching gel is directly proportional to this residence time. The bleaching effect can be accelerated by applying a heat lamp, a high intensity lamp such as a xenon arc lamp or other similar device or laser light to the gel once it is in place on the teeth.

Once the treatment is done, the gel is removed with a gauze or some other means and the patient's mouth is thoroughly cleaned with water and suction. Generally, with higher strength bleaching gels, only one or two such treatments are necessary.

The following examples are illustrative of the invention:

EXAMPLE 1

Two 12% urea peroxide dental bleaching gels were prepared. The first containing Carbopol® ETD™ 2020 as the thickening agent and the second containing Carbopol® 940 as the thickening agent. The components and concentrations used to make each dental bleaching gel are set forth below:

TABLE 5

Gel #1 - 12% Urea Peroxide Bleaching Gel using Carbopol ® ETD ™ 2020

| Component | % w/w |
| --- | --- |
| Glycerin 99.7% | 61.062 |
| Carbopol ® ETD ™ 2020 | 2.920 |
| Watermelon Flavor | 0.008 |
| Trolamine | 1.450 |
| Sodium Citrate Dihydrate | 13.270 |
| Urea Peroxide | 12.000 |
| Papain | 0.290 |
| Alumina | 4.000 |
| Potassium Nitrate | 5.000 |
| Total | 100.000 |

TABLE 6

Gel #2 - 12% Urea Peroxide Bleaching Gel using Carbopol ® 940

| Component | % w/w |
| --- | --- |
| Glycerin 99.7% | 61.062 |
| Carbopol ® 940 | 2.920 |
| Watermelon Flavor | 0.008 |
| Trolamine | 1.450 |
| Sodium Citrate Dihydrate | 13.270 |
| Urea Peroxide | 12.000 |
| Papain | 0.290 |
| Alumina | 4.000 |
| Potassium Nitrate | 5.000 |
| Total | 100.000 |

In addition, two 18% urea peroxide dental bleaching gels were prepared. The first containing Carbopol® ETD™ 2020 as the thickening agent and the second containing Carbopol® 940 as the thickening agent. The components and concentrations used to make each dental bleaching gel are set forth below:

TABLE 7

Gel #3 - 18% Urea Peroxide Bleaching Gel using Carbopol ® ETD ™ 2020

| Component | % w/w |
| --- | --- |
| Glycerin 99.7% | 55.062 |
| Carbopol ® ETD ™ 2020 | 2.920 |
| Watermelon Flavor | 0.008 |
| Trolamine | 1.450 |
| Sodium Citrate Dihydrate | 13.270 |
| Urea Peroxide | 18.000 |
| Papain | 0.290 |
| Alumina | 4.000 |
| Potassium Nitrate | 5.000 |
| Total | 100.000 |

TABLE 8

Gel #4 - 18% Urea Peroxide Bleaching Gel using Carbopol ® 940

| Component | % w/w |
| --- | --- |
| Glycerin 99.7% | 55.062 |
| Carbopol ® ETD ™ 940 | 2.920 |
| Watermelon Flavor | 0.008 |
| Trolamine | 1.450 |
| Sodium Citrate Dihydrate | 13.270 |
| Urea Peroxide | 18.000 |
| Papain | 0.290 |
| Alumina | 4.000 |
| Potassium Nitrate | 5.000 |
| Total | 100.000 |

Finally, two 40% urea peroxide dental bleaching gels were prepared. The first containing Carbopol® ETD™ 2020 as the thickening agent and the second containing Carbopol® 940 as the thickening agent. The components and concentrations used to make each dental bleaching gel are set forth below:

TABLE 9

Gel #5 - 40% Urea Peroxide Bleaching Gel using Carbopol ® ETD ™ 2020

| Component | % w/w |
| --- | --- |
| Glycerin 99.7% | 31.580 |
| Carbopol ® ETD ™ 2020 | 2.920 |
| Wintergreen Flavor | 1.490 |
| Trolamine | 1.450 |
| Sodium Citrate Dihydrate | 13.270 |
| Urea Peroxide | 40.000 |
| Papain | 0.290 |
| Alumina | 4.000 |
| Potassium Nitrate | 5.000 |
| Total | 100.000 |

TABLE 10

Gel #5 - 40% Urea Peroxide Bleaching Gel using Carbopol ® ETD ™ 2020

| Component | % w/w |
|---|---|
| Glycerin 99.7% | 31.580 |
| Carbopol ® ETD ™ 940 | 2.920 |
| Wintergreen Flavor | 1.490 |
| Trolamine | 1.450 |
| Sodium Citrate Dihydrate | 13.270 |
| Urea Peroxide | 40.000 |
| Papain | 0.290 |
| Alumina | 4.000 |
| Potassium Nitrate | 5.000 |
| Total | 100.000 |

Viscosity data were then measured for each of the aforementioned gels numbered 1, 2, 3, 4, 5, and 6. The results of these measurements are set forth in FIG. 1.

FIG. 1 is a bar graph of viscosity in centipoise (cps) as a function of gel type. As can be seen, the gels utilizing Carbopol® 940 exhibited very low viscosity. The 12% urea peroxide gel employing Carbopol® 940 had a viscosity of 35,300 cps, the 18% urea peroxide gel employing Carbopol® 940 had a viscosity of 67,500 cps, and the 40% urea peroxide gel employing Carbopol® 940 had a viscosity of 169,000 cps. All of the viscosity measurements were taken with a Brookfield DV-II viscometer using T-Bar Spindle # 91 at 5 rpm. None of the gels employing Carbopol® 940 exhibited a viscosity higher than 400,000 cps.

In contrast, as can be seen in FIG. 1, the gels utilizing Carbopol® ETD™ 2020 exhibited much higher viscosities. The 12% urea peroxide gel employing Carbopol® ETD™ 2020 exhibited a viscosity of 422,500 cps, the 18% urea peroxide gel employing Carbopol® ETD™ 2020 exhibited a viscosity of 2,190,000 cps, and the 40% urea peroxide gel exhibited a viscosity of 3,030,000 cps. The viscosity measurements on the 12% and 40% gels were taken with T-Bar Spindles #93 and 95, respectively, at 5 rpm. The viscosity measurement on the 18% gel was taken with T-Bar Spindle # 91 at 0.5 rpm. All of the gels employing Carbopol® ETD™ 2020 exhibited a viscosity above 400,000 cps.

While the invention has been described in conjunction with the specific embodiments outlined above, it is evident that many alternatives, modifications, and variations will be apparent to those skilled in the art. Accordingly, the preferred embodiments of the invention are intended to be illustrative and not limiting. Various changes may be made without departing from the spirit and scope of the invention as defined in the claims.

What is claimed is:

1. A substantially anhydrous dental bleaching gel contained in a sealed dispensing container comprising: (i) at least 25% by weight of organic polyol; (ii) less than 3% by weight polyacrylic acid thickening agent; (iii) at least 3% by weight of a bleaching peroxide that releases oxygen gas; (iv) neutralizing agent; (v) chelating agent; and (vi) desensitizing agent; wherein said chelating agent imparts greater peroxide stability such that there is a reduction in oxygen gas generation and, therefore, a reduction in container leaks.

2. The dental bleaching gel of claim 1 wherein the gel contains no more than 2% by weight water.

3. The dental bleaching gel of claim 1 wherein the organic polyol is glycerin.

4. The dental bleaching gel of claim 1 wherein the polyacrylic acid thickening agent is a carbomer.

5. The dental bleaching gel of claim 1 wherein the polyacrylic acid thickening agent is a carbomer and wherein a 500 gram dispersion containing said carbomer in an amount of 0.5% by weight (2.5 grams) takes only about 5 minutes to completely wet without mixing.

6. The dental bleaching gel of claim 1 wherein the bleaching agent is hydrogen peroxide or a compound that releases hydrogen peroxide upon exposure to water.

7. The dental bleaching gel of claim 1 wherein the bleaching agent is urea peroxide.

8. The dental bleaching gel of claim 1 wherein the neutralizing agent is a base selected from the group consisting of alkali metal hydroxides and ammonium hydroxide, carbonates, alkoxides, oxides, peroxides, superoxides, water soluble amines, and amino acids.

9. The dental bleaching gel of claim 1 wherein the neutralizing agent is selected from the group consisting of sodium hydroxide, potassium hydroxide, ammonium hydroxide, triethanolamine, aminomethylpropanol, 2-amino-2-hydroxymethyl-1,3-propanediol, tetrahydroxypropyl ethylenediamine, and tris(hydroxymethyl) aminomethane.

10. The dental bleaching gel of claim 1, wherein said desensitizing agent is present in an amount of 0.1 to 10% by weight.

11. The dental bleaching gel of claim 1 wherein said desensitizing agent is selected from the group consisting of alkali and alkaline earth metal salts of an organic acid or halide.

12. The dental bleaching gel of claim 1 wherein said desensitizing agent is selected from the group consisting of alkali and alkaline earth metal salts of nitric acid, citric acid and halides.

13. The dental bleaching gel of claim 1 wherein said desensitizing agent is selected from the group consisting of potassium nitrate, strontium chloride, potassium citrate and strontium nitrate.

14. The dental bleaching gel of claim 1 wherein the chelating agent additionally serves as a peroxide stabilizer.

15. The method of claim 1 wherein the chelating agent is selected from the group consisting of EDTA, CDTA and salts thereof.

* * * * *